(12) United States Patent
Creasey et al.

(10) Patent No.: US 10,335,028 B2
(45) Date of Patent: *Jul. 2, 2019

(54) OPHTHALMOLOGY (71) Applicant: Optos PLC, Dunfermline, Fife, Scotland (GB)

(72) Inventors: Christopher David Creasey, Cambridge (GB); Stuart Brian Milne, Cambridge (GB); Andrew Fogg, Great Gransden (GB)

(73) Assignee: Optos PLC, Dunfermline (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/924,106

(22) Filed: Mar. 16, 2018

(65) Prior Publication Data

US 2018/0199811 A1 Jul. 19, 2018

Related U.S. Application Data

(63) Continuation of application No. 15/001,676, filed on Jan. 20, 2016, now Pat. No. 9,949,638, which is a
(Continued)

(30) Foreign Application Priority Data

Jan. 13, 2011 (GB) .................................. 1100555.0

(51) Int. Cl.
*A61B 3/14* (2006.01)
*A61B 3/10* (2006.01)
(Continued)

(52) U.S. Cl.
CPC .............. *A61B 3/12* (2013.01); *A61B 3/0008* (2013.01); *A61B 3/1025* (2013.01); *A61B 3/14* (2013.01);
(Continued)

(58) Field of Classification Search
CPC .. A61B 3/00; A61B 3/103; A61B 3/02; A61B 3/113; A61B 3/1015; A61B 3/1225;
(Continued)

(56) References Cited

U.S. PATENT DOCUMENTS 4,213,678 A 7/1980 Pomerantzeff et al.
4,772,114 A 9/1988 Fukui et al.
(Continued)

FOREIGN PATENT DOCUMENTS

CN 101489468 A 7/2009
GB 2440163 1/2008
(Continued)

OTHER PUBLICATIONS

Search Report for CN 201180064856X dated Nov. 11, 2014.
(Continued)

*Primary Examiner* — Dawayne Pinkney
(74) *Attorney, Agent, or Firm* — Pavan K. Agarwal; Shabbi S. Khan; Foley & Lardner LLP (57) ABSTRACT

Apparatus for illuminating the retina of an eye. The apparatus includes an illumination device and a lens system. The illumination device and the lens system combine to provide incident illumination from an apparent point source located within the lens system. The apparatus also includes an illumination transfer device. The illumination transfer device has two foci and the apparent point source of the lens system is provided at a first focus point of the illumination transfer device and an eye is accommodated at a second focus point of the illumination transfer device. The illumination transfer device transfers the incident illumination from the apparent point source into the eye to illuminate the retina.

14 Claims, 3 Drawing Sheets

Related U.S. Application Data continuation of application No. 13/978,849, filed as application No. PCT/GB2011/052458 on Dec. 12, 2011, now abandoned.

(51) Int. Cl.

| | | |
|---|---|---|
| *A61B 3/00* | (2006.01) | |
| *A61B 3/12* | (2006.01) | |
| *A61N 5/06* | (2006.01) | |
| *A61F 9/008* | (2006.01) | |
| *G02B 26/08* | (2006.01) | |
| *G02B 26/10* | (2006.01) | |

(52) U.S. Cl.
CPC ............... *A61F 9/008* (2013.01); *A61N 5/06* (2013.01); *G02B 26/0833* (2013.01); *G02B 26/101* (2013.01); *A61F 2009/00897* (2013.01)

(58) Field of Classification Search
CPC ......... A61B 3/111; A61B 3/08; A61B 3/0285; A61B 3/1208; A61B 3/032; A61B 3/024; G02C 13/005
USPC ....... 351/200, 202, 205, 221, 246, 210, 204, 351/201, 209, 211, 218, 222–226
See application file for complete search history.

(56) References Cited

U.S. PATENT DOCUMENTS

| | | |
|---|---|---|
| 5,493,109 A | 2/1996 | Wei et al. |
| 5,815,242 A | 9/1998 | Anderson et al. |
| 6,081,304 A | 6/2000 | Kuriyama et al. |
| 6,690,516 B2 | 2/2004 | Aritake et al. |
| 7,068,444 B2 | 6/2006 | Nishi |
| 7,275,826 B2 | 10/2007 | Liang |
| 2002/0101568 A1 | 8/2002 | Eberl et al. |
| 2006/0072215 A1 | 4/2006 | Nishi |
| 2007/0030449 A1 | 2/2007 | Liang |
| 2007/0109619 A1 | 5/2007 | Eberl et al. |
| 2007/0285793 A1 | 12/2007 | Liu et al. |
| 2008/0151185 A1 | 6/2008 | Saito et al. |
| 2010/0141895 A1 | 6/2010 | Cairns et al. |
| 2010/0149073 A1 | 6/2010 | Chaum et al. |
| 2010/0328606 A1 | 12/2010 | Peyman |
| 2012/0133888 A1 | 5/2012 | Gray et al. |

FOREIGN PATENT DOCUMENTS

| | | |
|---|---|---|
| JP | S59-006029 A | 1/1984 |
| JP | S61-052850 A | 3/1986 |
| JP | S61-206422 | 12/1986 |
| JP | S62-008730 A | 1/1987 |
| JP | H05-309072 A | 11/1993 |
| JP | H09-509337 A | 9/1997 |
| JP | 2001-290102 A | 10/2001 |
| JP | 2002-520006 | 7/2002 |
| JP | 2005-501587 | 1/2005 |
| JP | 2006-095318 | 4/2006 |
| JP | 2006-230799 A | 9/2006 |
| JP | 2009-119153 | 6/2009 |
| JP | 4287375 B2 | 7/2009 |
| JP | 2009-543585 | 12/2009 |
| JP | 2010-508932 A | 3/2010 |
| JP | 2012-525184 A | 10/2012 |
| WO | WO-95/13012 A2 | 5/1995 |
| WO | WO-2009/084842 | 7/2009 |
| WO | WO-2010/125394 | 11/2010 |

OTHER PUBLICATIONS

Search Report for JP 2013-548882 dated Sep. 17, 2015, with English translation.
Submission of Publications for JP 2013-548882 submitted Mar. 4, 2015, with English translation.
English translation of the First Chinese Office Action dated Nov. 18, 2014 for Chinese Patent Appln. No. 201180064856.
English Translation of the Second Chinese Office Action dated May 28, 2015 in connection with Chinese Patent Appln. No. 201180064856.
English Translation of the Third Chinese Office Action dated Feb. 3, 2016 in connection with Chinese Patent Appln. No. 201180064856.
European Office Action dated Aug. 6, 2015 in European Patent Application No. 11808912.7.
International Preliminary Report on Patentability dated Jul. 16, 2013 in PCT Application No. PCT/GB2011/52458.
International Search Report and Written Opinion dated Mar. 19, 2012 in PCT Application No. PCT/GB2011/52458.
U.S. Office Action in U.S. Appl. No. 13/978,849 dated Jan. 22, 2015.
U.S. Office Action in U.S. Appl. No. 13/978,849 dated Jul. 20, 2015.
U.S. Office Action in U.S. Appl. No. 15/001,676 dated Apr. 20, 2016.
U.S. Office Action in U.S. Appl. No. 15/001,676 dated Sep. 6, 2016.
U.S. Office Action in U.S. Appl. No. 15/001,676 dated Aug. 24, 2017.
Notice of Allowance for U.S. Appl. No. 15/001,676 dated Dec. 20, 2017.
Friberg, Thomas R. et al., "Non-Mydriatic Panoramic Fundus Imaging Using a Non-Contact Scanning Laser-Based System", Ophthalmic Surgery, Laser and Imaging, vol. 34, No. 6, Nov. 1, 2003, pp. 488-497.
Notification of Reasons for Refusal for Application No. 2017-156394 dated Aug. 21, 2018.

OPHTHALMOLOGY

This patent application is a continuation of U.S. patent application Ser. No. 15/001,676, which is a continuation of U.S. patent application Ser. No. 13/978,849. U.S. patent application Ser. No. 13/978,849 is a national-stage filing of International Patent Application No. PCT/GB2011/052458 and. All of the foregoing applications are herein incorporated by reference.

The present invention relates to an apparatus and method for illuminating, imaging and treating the retina of a human eye.

Imaging systems, such as scanning laser ophthalmoscopes (SLOs), may comprise a large number of optical components, such as laser scanning elements, scan transfer mirrors, laser sources and detectors. The laser scanning arrangement consists of first and second orthogonal scanning elements, which typically include a high speed rotating polygonal mirror and a motor driven slow speed mirror. These elements are used to create a raster scan pattern of the human retina. The polygon mirror has a plurality of facets and typically provides the vertical scanning of the laser beam, and the slow speed mirror typically provides the horizontal scanning of the laser beam. The scan transfer mirror transfers the two dimensional laser scan pattern created by the scanning elements to the retina of the eye.

While such imaging systems provide acceptable images of the retina of the eye, they are limited in that they are expensive to manufacture (the laser scanning elements and scan transfer mirror are particularly expensive components), large in size and, due to the large number of optical components, have low optical efficiency.

According to a first aspect of the present invention there is provided an apparatus for illuminating the retina of an eye comprising:
an illumination device;
a lens system,
wherein the illumination device and the lens system combine to provide incident illumination from an apparent point source located within the lens system; and
an illumination transfer device, wherein the illumination transfer device has two foci and the apparent point source of the lens system is provided at a first focus point of the illumination transfer device and an eye is accommodated at a second focus point of the illumination transfer device, and wherein the illumination transfer device transfers the incident illumination from the apparent point source into the eye to illuminate the retina.

The lens system may include an apparent focus point located within the lens system. The lens system may comprise a plurality of lens elements. The apparent focus point may be located within an outermost lens element of the lens system. The apparent focus point and the apparent point source are coincident.

The illumination device and the lens system combine to illuminate an area of the retina. That is, the illumination device and the lens system are capable of illuminating a two-dimensional portion of the retina.

The pupillary point of the eye may be accommodated at the second focus of the illumination transfer device.

The front nodal point of the eye may be accommodated at the second focus of the illumination transfer device.

The illumination device and the lens system are arranged such that the apparent point source is stationary. This ensures that the maximum incident illumination is transferred into the eye at the pupillary point.

The lens system may include a wide-angle lens. The wide-angle lens may have a field of view (FOV) of between 30 degrees and 180 degrees. Preferably the wide-angle lens has a FOV of between 90 degrees and 160 degrees. More preferably, the wide-angle lens has a FOV of 120 degrees. The lens system may comprise or consist of a fisheye lens.

The lens system may comprise a plurality of lens elements. The lens system may comprise any number and/or type of lenses required to achieve the desired FOV and/or to achieve achromatism across the visible spectrum.

The apparent point source may be located within any one of the plurality of lens elements. Preferably, the apparent point source is located in the outermost lens element facing the illumination transfer device.

The illumination transfer device may comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

The apparatus may further comprise an illumination relay device. The illumination relay device may comprise two foci. One foci of the illumination relay device may be coincident with one foci of the illumination transfer device and the other foci of the illumination relay device may be coincident with the apparent point source of the illumination device and the lens system. In this arrangement, the illumination relay device is placed between the illumination transfer device and the lens system. The illumination device and the lens system again combine to provide incident illumination from an apparent point source located within the lens system, the apparent point source is located at the first focus point of the illumination relay device and the second focus of the illumination relay device is coincident with the first focus of the illumination transfer device. The retina of the eye is again illuminated by the illumination transfer device transferring the illumination from its first focus point to the pupillary point of the eye at its second focus.

The illumination relay device may comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

The illumination relay device may have the same geometry as the illumination transfer device.

The illumination relay device has a major axis, which lies on a line joining the two foci. The illumination transfer device also has a major axis, which lies on a line joining the two foci. The illumination transfer device and the illumination relay device may be arranged such that the major axis of each device are parallel and/or collinear. This arrangement corrects for distortions introduced by the illumination transfer device. Since the geometry of the illumination relay device is the same as the geometry of the illumination transfer device, the distortions can be cancelled out, or at least partially corrected for.

The illumination device may include a light source. The light source may provide collimated light.

The light source may include a laser, a light emitting diode (LED), a Vertical Cavity Surface Emitting Laser (VCSEL), a super luminescent diode (SLD), a diode laser, a collimated incandescent lamp, a flash or illumination device or a digital light processing (DLP) projection device.

The light source may provide illumination at one or more differing wavelengths. The light source may provide red light illumination (approximately 650 nm) and/or green light illumination (approximately 510 nm).

The light source may be adapted to provide light at a wavelength between 450 nm and 1000 nm. Preferably, the light source may be adapted to provide light at a wavelength between 488 nm and 700 nm. More preferably, the light source provides light at a wavelength of between 515 nm and 650 nm.

The light source may be adapted to provide light at a power of between 500 nWatt and 1 W.

The light source may include one or more light sources of differing wavelengths.

The light source may be configured such that the wavelength of light provided is variable.

The light source may be configured such that the power of light provided is variable.

The illumination device may include a two-dimensional scanning device for scanning the retina of the eye with collimated light. In this configuration, the illumination device and the lens system combine to provide a two-dimensional collimated light scan from the apparent point source located within the lens system.

The two-dimensional scanning device may comprise a first scanning element and a second scanning element.

The first and second scanning elements may comprise an oscillating mechanism. The oscillating mechanism may be a resonant scanner.

The first and second scanning elements may comprise an oscillating plane mirror. The oscillating plane mirror may be a galvanometer mirror.

The first and second scanning elements may comprise a rotating mechanism. The rotating mechanism may be a rotating polygon mirror.

The first and second scanning elements may comprise a line scanning element. The line scanning element may comprise a laser line scanner. The laser line may be generated by a diffractive optical element, cylindrical lens, or other known means of creating a laser line.

The first and second scanning elements may comprise a combination of oscillating mechanisms, rotating mechanisms or line scanning elements, as described above.

The two-dimensional scanning device may be a microelectromechanical system (MEMS) scanning element having two axes of rotation. However, it should be appreciated that the two-dimensional scanning device may be any suitable device which is capable of rotating in at least two axes, which are preferably orthogonal. The scanning device should preferably be capable of operating at high speed (i.e. above 5 kHz) and provide a high amplitude of scan (i.e. up to 180 degrees or more).

The illumination device may further comprise one or more detectors for detecting the reflected light from the retina. The reflected light from the retina may be used to form an image of the retina.

The light detector may include fast photo detectors, such as avalanche photo diodes (APDs), PIN diodes, photomultiplier tubes (PMT), silicon photo multipliers (SPM), or similar single point detectors.

The apparatus may further comprise one or more data processing devices for displaying, storing and/or combining the obtained images of the retina.

The apparatus may be pivotable between a first position, in which the apparatus may be used to illuminate the first retina of a first eye, and a second position, in which the apparatus may be used to illuminate the second retina of a second eye.

According to a second aspect of the invention, there is provided a system for illuminating the retina of each eye of a patient comprising two apparatuses according to the first aspect of the invention, wherein each apparatus may be capable of illuminating the retina of one eye.

According to a third aspect of the present invention there is provided a method of illuminating the retina of an eye comprising the steps of:
providing an illumination device;
providing a lens system;
using the illumination device and the lens system in combination to provide incident illumination from an apparent point source located within the lens system;
providing an illumination transfer device having two foci;
providing the apparent point source at the first focus point of the illumination transfer device and an eye at the second focus point of the illumination transfer device; and
using the illumination transfer device to transfer the incident illumination from the apparent point source into the eye.

The lens system may include an apparent focus point located within the lens system. The lens system may comprise a plurality of lens elements. The apparent focus point may be located within an outermost lens element of the lens system. The apparent focus point and the apparent point source are coincident.

The illumination device and the lens system combine to illuminate an area of the retina. That is, the illumination device and the lens system are capable of illuminating a two-dimensional portion of the retina.

The pupillary point of the eye may be accommodated at the second focus of the illumination transfer device.

The front nodal point of the eye may be accommodated at the second focus of the illumination transfer device.

The illumination device and the lens system are arranged such that the apparent point source is stationary. This ensures that the maximum incident illumination is transferred into the eye at the pupillary point.

The lens system may include a wide-angle lens. The wide-angle lens may have a field of view (FOV) of between 30 degrees and 180 degrees. Preferably the wide-angle lens has a FOV of between 90 degrees and 160 degrees. More preferably, the wide-angle lens has a FOV of 120 degrees. The lens system may comprise or consist of a fisheye lens.

The lens system may comprise a plurality of lens elements.

The apparent point source may be located within any one of the plurality of lens elements. Preferably, the apparent point source is located in the outermost lens element facing the illumination transfer device.

The illumination transfer device may comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

The method may comprise the further step of providing an illumination relay device comprising two foci. One foci of the illumination relay device may be coincident with one foci of the illumination transfer device and the other foci of the illumination relay device may be coincident with the apparent point source of the illumination device and the lens system. In this arrangement, the illumination relay device is placed between the illumination transfer device and the lens system. The illumination device and the lens system again combine to provide incident illumination from an apparent point source located within the lens system, the apparent point source is located at the first focus point of the illumination relay device and the second focus of the illumination relay device is coincident with the first focus of the illumination transfer device. The retina of the eye is again illuminated by the illumination transfer device transferring the illumination from its first focus point to the pupillary point of the eye at its second focus.

The illumination relay device may comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

The illumination relay device may have the same geometry as the illumination transfer device.

The illumination relay device has a major axis, which lies on a line joining the two foci. The illumination transfer device also has a major axis, which lies on a line joining the two foci. The illumination transfer device and the illumination relay device may be arranged such that the major axes of each device are parallel and/or collinear. This arrangement corrects for distortions introduced by the illumination transfer device. Since the geometry of the illumination relay device is the same as the geometry of the illumination transfer device, the distortions can be cancelled out, or at least partially corrected for.

The illumination device may include a light source. The light source may provide collimated light.

The light source may include a laser, a light emitting diode (LED), a Vertical Cavity Surface Emitting Laser (VCSEL), a super luminescent diode (SLD), a diode laser, a collimated incandescent lamp, a flash or illumination device or a digital light processing (DLP) projection device.

The light source may provide illumination at one or more differing wavelengths. The light source may provide red light illumination (approximately 650 nm) and/or green light illumination (approximately 510 nm).

The light source may be adapted to provide light at a wavelength between 450 nm and 1000 nm. Preferably, the light source may be adapted to provide light at a wavelength between 488 nm and 700 nm. More preferably, the light source provides light at a wavelength of between 515 nm and 650 nm.

The light source may be adapted to provide light at a power of between 500 nWatt and 1 W.

The light source may include one or more light sources of differing wavelengths.

The light source may be configured such that the wavelength of light provided is variable.

The light source may be configured such that the power of light provided is variable.

The illumination device may include a two-dimensional scanning device for scanning the retina of the eye with collimated light. In this configuration, the illumination device and the lens system combine to provide a two-dimensional collimated light scan from the apparent point source located within the lens system.

The two-dimensional scanning device may comprise a first scanning element and a second scanning element.

The first and second scanning elements may comprise an oscillating mechanism. The oscillating mechanism may be a resonant scanner.

The first and second scanning elements may comprise an oscillating plane mirror. The oscillating plane mirror may be a galvanometer mirror.

The first and second scanning elements may comprise a rotating mechanism. The rotating mechanism may be a rotating polygon mirror.

The first and second scanning elements may comprise a line scanning element. The line scanning element may comprise a laser line scanner. The laser line may be generated by a diffractive optical element, cylindrical lens, or other known means of creating a laser line.

The first and second scanning elements may comprise a combination of oscillating mechanisms, rotating mechanisms or line scanning elements, as described above.

The two-dimensional scanning device may be a microelectromechanical system (MEMS) scanning element having two axes of rotation. However, it should be appreciated that the two-dimensional scanning device may be any suitable device which is capable of rotating in at least two axes, which are preferably orthogonal. The scanning device should preferably be capable of operating at high speed (i.e. above 5 kHz) and provide a high amplitude of scan (i.e. up to 180 degrees or more).

The method may comprise the further step of providing one or more light detectors and using the one or more light detectors to detect reflected light from the retina to form an image of the retina. In this arrangement the method performs the steps of illuminating the retina and obtaining an image of the retina.

The light detector may include fast photo detectors, such as avalanche photo diodes (APDs), PIN diodes, photomultiplier tubes (PMT), silicon photo multipliers (SPM), or similar single point detectors.

The method may comprise the further step of pivoting the illumination device, lens system and illumination transfer device between a first position, in which illumination of the first retina of a first eye is performed, and a second position, in which illumination of the second retina of a second eye is performed.

According to a fourth aspect of the present invention there is provided an apparatus for imaging the retina of an eye comprising:
    an illumination device;
    a lens system,
    wherein the illumination device and the lens system combine to provide incident illumination from an apparent point source located within the lens system;
    a light detector; and
    an illumination transfer device, wherein the illumination transfer device has two foci and the apparent point source of the lens system is provided at a first focus point of the illumination transfer device and an eye is accommodated at a second focus point of the illumination transfer device, and wherein the illumination transfer device transfers the incident illumination from the apparent point source into the eye to illuminate the retina and the light detector detects light reflected from the retina to obtain an image of the retina.

According to a fifth aspect of the present invention there is provided a method of imaging the retina of an eye comprising the steps of:
    providing an illumination device;
    providing a lens system;
    using the illumination device and the lens system in combination to provide incident illumination from an apparent point source located within the lens system;
    providing a light detector;
    providing an illumination transfer device having two foci;

providing the apparent point source at the first focus point of the illumination transfer device and an eye at the second focus point of the illumination transfer device;

using the illumination transfer device to transfer the incident illumination from the apparent point source into the eye; and using the light detector to detect light reflected from the retina to produce an image of the retina.

According to a sixth aspect of the present invention there is provided an apparatus for treating the retina of an eye with collimated light comprising:

a collimated light illumination device;

a lens system, wherein the illumination device and the lens system combine to provide incident collimated light illumination from an apparent point source located within the lens system; and an illumination transfer device, wherein the illumination transfer device has two foci and the apparent point source of the lens system is provided at a first focus point of the illumination transfer device and an eye is accommodated at a second focus point of the illumination transfer device, and wherein the illumination transfer device transfers the incident collimated light illumination from the apparent point source into the eye.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

According to a seventh aspect of the present invention there is provided a method of treating the retina of an eye with collimated light comprising the steps of:

providing a collimated light illumination device;

providing a lens system;

using the illumination device and the lens system in combination to provide incident collimated light illumination from an apparent point source located within the lens system;

providing an illumination transfer device having two foci;

providing the apparent point source at the first focus point of the illumination transfer device and an eye at the second focus point of the illumination transfer device; and using the illumination transfer device to transfer the incident collimated light illumination from the apparent point source into the eye.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

Embodiments of the present invention will now be described, by way of example only, with reference to the accompanying drawings, in which.

Figure 1:
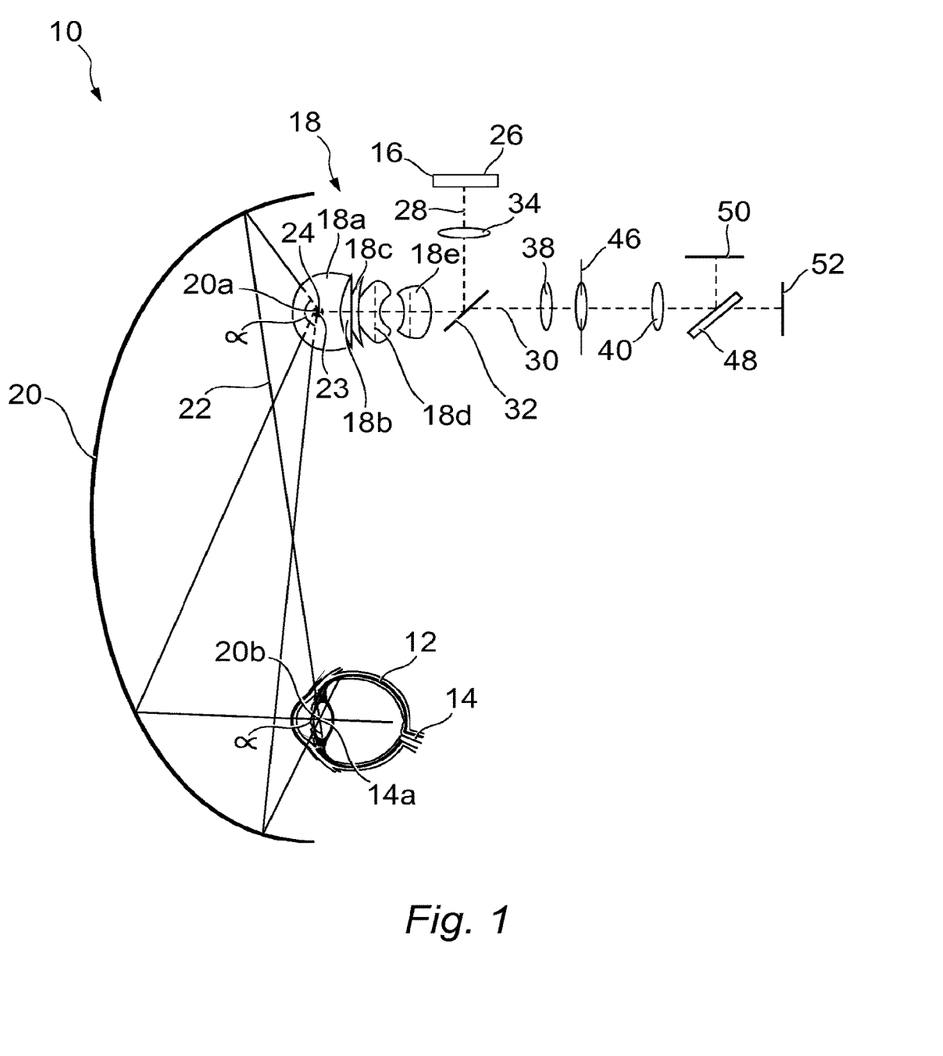
FIG. 1 is a schematic side view of an apparatus for illuminating, imaging and treating the retina of an eye according to the present invention.

FIG. 1 illustrates an apparatus 10 for illuminating the retina 12 of an eye 14. The apparatus 10 includes an illumination device 16, a lens system 18 and an illumination transfer device 20.

The lens system 18 is arranged to include an apparent focus point 23 located within the lens system 18. The illumination device 16 and the lens system 18 are arranged such that they combine to provide incident illumination 22 from an apparent point source 24 located within the lens system 18. The apparent focus point 23 of the lens system 18 is coincident with the apparent point source 24 of the lens system 18. The focus point 23 and point source 24 are termed "apparent" because when the illumination device 16 illuminates the lens system 18 it appears that the incident illumination 22 emanates from an actual, or "real", point located within the system. That is, if the incident illumination 22 were traced back into the lens system 18 without any refraction, it would appear as if it were emanating from a single point. This is, of course, not true with a wide-angle lens, hence the term "apparent" for both focus point and point source is used. Importantly, the apparent point source 24 is stationary with respect to the lens system 18. This ensures that the incident illumination 22 emanates from the apparent point source 24 without translation.

The incident illumination 22 generated by the illumination device 16 and the lens system 18 is two-dimensional and therefore illuminates an area of the retina 12 (see below). The incident illumination 22 in the embodiment illustrated and described here provides a "flood illumination", i.e. the illumination device 16 simultaneously illuminates the area of the retina.

The illumination device 16 includes a light source 26. The light source 26 may provide collimated light. The light source 26 may include a laser, a light emitting diode (LED), a Vertical Cavity Surface Emitting Laser (VCSEL), a super luminescent diode (SLD), a diode laser, a collimated incandescent lamp, a flash or illumination device or a digital light processing (DLP) projection device.

The light source 26 is capable of providing illumination at one or more differing wavelengths. In this arrangement, the light source 26 may provide red light illumination (approximately 650 nm) and/or green light illumination (approximately 510 nm). The light source 26 is capable of providing light at a power of between 500 nWatt and 1 W. The wavelength and power of the light from the light source 26 may both be variable.

As illustrated in FIG. 1, the lens system 18 includes an incident optical path 28 and a return optical path 30. The incident optical path 28 and a return optical path 30 are split by a beam splitter 32. The beam splitter 32 illustrated and described here is 80:20 transmission/reflection. However, it should be appreciated that other types of beam splitters could be used if required.

The incident optical path 28 includes a first focussing lens 34 and the return optical path 30 includes second and third focussing lenses 38, 40 and a combined focussing lens and aperture 46. In the embodiment illustrated and described here the return optical path 30 also includes a second (dichroic) beam splitter 48 which splits the returned reflected light from the retina 12 to a first detector 50 and a second detector 52. As described below, the first detector 50 detects red light and the second detector 52 detects green light. It should, however, be appreciated that the apparatus 10 may not necessarily need to include two separate colour detectors and that the apparatus 10 may function equally well with a single detector.

In the embodiment described and illustrated here the lens system 18 is a wide-angle lens system which may consist or comprise a fisheye lens. The lens system 18 is a wide-angle lens comprising a plurality of meniscus lens elements 18a to 18e. The wide-angle lens may have a field of view (FOV) of between 30 degrees and 180 degrees. Preferably, the FOV is around 120 degrees. However, it should be appreciated that the wide-angle lens may have a FOV at any suitable angle between the above-referenced range depending on the specific requirements of the apparatus 10.

The illumination device 16 and the lens system 18 are arranged such the incident illumination 22 emanates from the apparent point source 24 at an angle α. Angle α is around 120 degrees (see FIG. 1).

The illumination transfer device 20 has two foci 20a, 20b. In the embodiment illustrated and described here the illumination transfer device 20 is an ellipsoidal mirror. However, it should be appreciated that the illumination transfer device 20 may alternatively comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

As illustrated in FIG. 1, the illumination transfer device 20 and the lens system 18 are arranged such that the apparent point source 24 is provided at the first focus point 20a of the illumination transfer device 20 and the eye 14 is accommodated at the second focus point 20b of the illumination transfer device 20. More specifically, the pupillary point 14a of the eye 14 is positioned at the second focus point 20b of the illumination transfer device 20.

The incident illumination 22 is conveyed to the subject's eye 14 via the illumination transfer device 20. The incident illumination 22 provided at the apparent point source 24 by the illumination device 16 and the lens system 18 is coupled by the illumination transfer device 20 through the pupillary point 14a of the subject's eye 14, and thus onto the retina 12. Thus, the apparatus 10 provides illumination of an area of the retina 12.

As stated above, the incident illumination 22 emanates from the apparent point source 24 without translation, i.e. the apparent point source 24 is stationary during operation. The result of this is that the incident illumination 22 emerging at the second focus point 20b of the illumination transfer device 20 is also stationary. The illumination transfer device 20 therefore provides "point-to-point" transfer of the incident illumination 22 without translation, or clipping, thereof. Since the illumination transfer device 20 provides point-to-point transfer of the incident illumination 22, the incident illumination 22 emerging at the second focus point 20b of the illumination transfer device 20 emanates therefrom with the same angle α that the incident illumination 22 emanates from the first focus point 20a of the illumination transfer device 20, i.e. at an angle of around 120 degrees.

The result of this is that the incident illumination 22 enters the eye without being "clipped" by the iris, for example. This maximises the area of the retina 12 that can be illuminated by the apparatus 10 and allows ultra-wide illumination of the retina 12 to be performed. As described above, the incident illumination 22 enters the pupillary point 14a of the subject's eye 14 at an angle of around 120 degrees. An angle of around 120 degrees at the pupillary point 14a of the eye 14 equates to an angle of around 200 degrees when measured at the centre of the eye 14. Therefore, the apparatus 10 can be considered as providing a 120 degree "external" angle of illumination and a 200 degree "internal" angle of illumination.

The above-described properties of the illumination device 16, the lens system 18 and the illumination transfer device 20 also ensures that reflected light from the retina is conveyed back through the same optical path of the apparatus 10.

Figure 3:
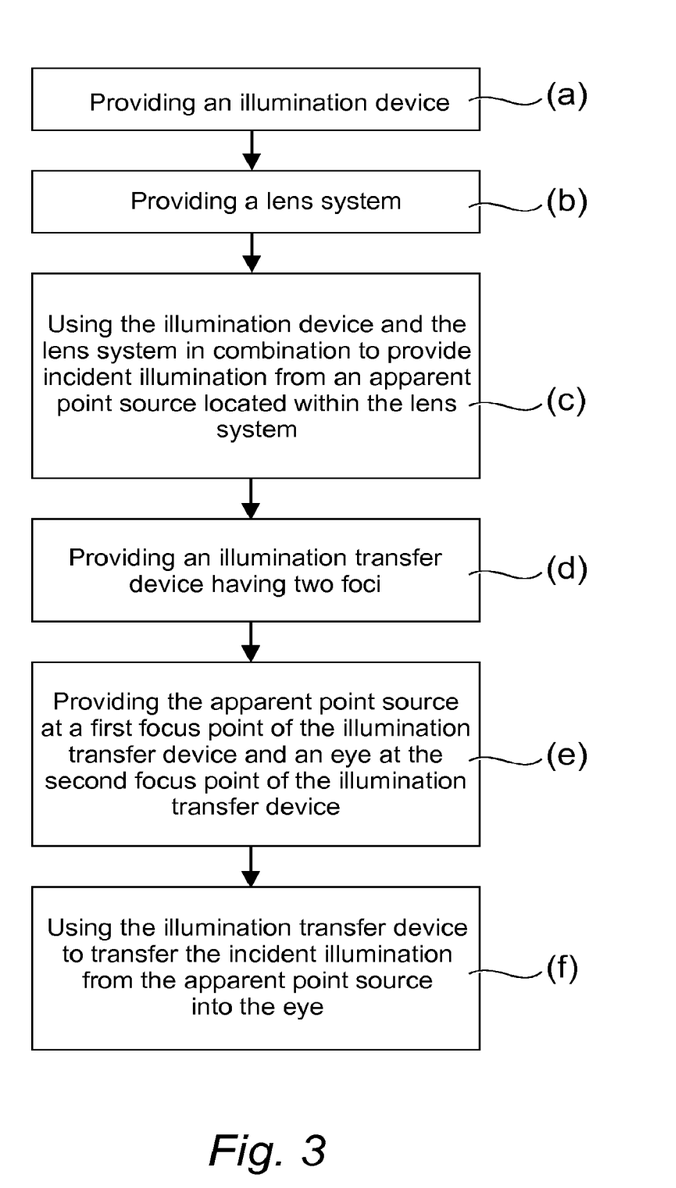
FIG. 3 is a flowchart diagram detailing a method of illuminating, imaging and treating the retina of an eye according to the present invention.

The process of illuminating the retina 12 of the eye 14 is illustrated in FIG. 3. With reference to FIG. 3, the retina 12 of the eye 14 may be illuminated by (a) providing the illumination device 16, (b) providing the lens system 18, (c) using the illumination device 16 and the lens system 18 in combination to provide incident illumination from the apparent point source 24 located within the lens system 18, (d) providing the illumination transfer device 20 having two foci 20a, 20b, (e) providing the apparent point source 24 at the first focus point 20a of the illumination transfer device 20 and an eye 14 at the second focus point 20b of the illumination transfer device 20 and (f) using the illumination transfer device 20 to transfer the incident illumination 22 from the apparent point source 24 into the eye 14.

As described above, the reflected light returned from the retina 12 is detected at the first and second detectors 50, 52. The reflected light returned from the retina 12 is used to produce an image of the subject's retina 12 in the known manner.

The detectors 50, 52 may include fast photo detectors, such as avalanche photo diodes (APDs), PIN diodes, photomultiplier tubes (PMTs), silicon photo multipliers (SPMs), or similar single point detectors.

The apparatus 10 also comprises a data processing device for displaying, processing, storing, and/or combining the obtained images of the retina 12. The apparatus 10 may also comprise a distortion correction device, which may be part of the data processing device, for correcting distortions introduced by the illumination transfer device 20. The apparatus 10 may also include on or more filed flattener elements which correct for focal aberrations in the system.

Figure 2:
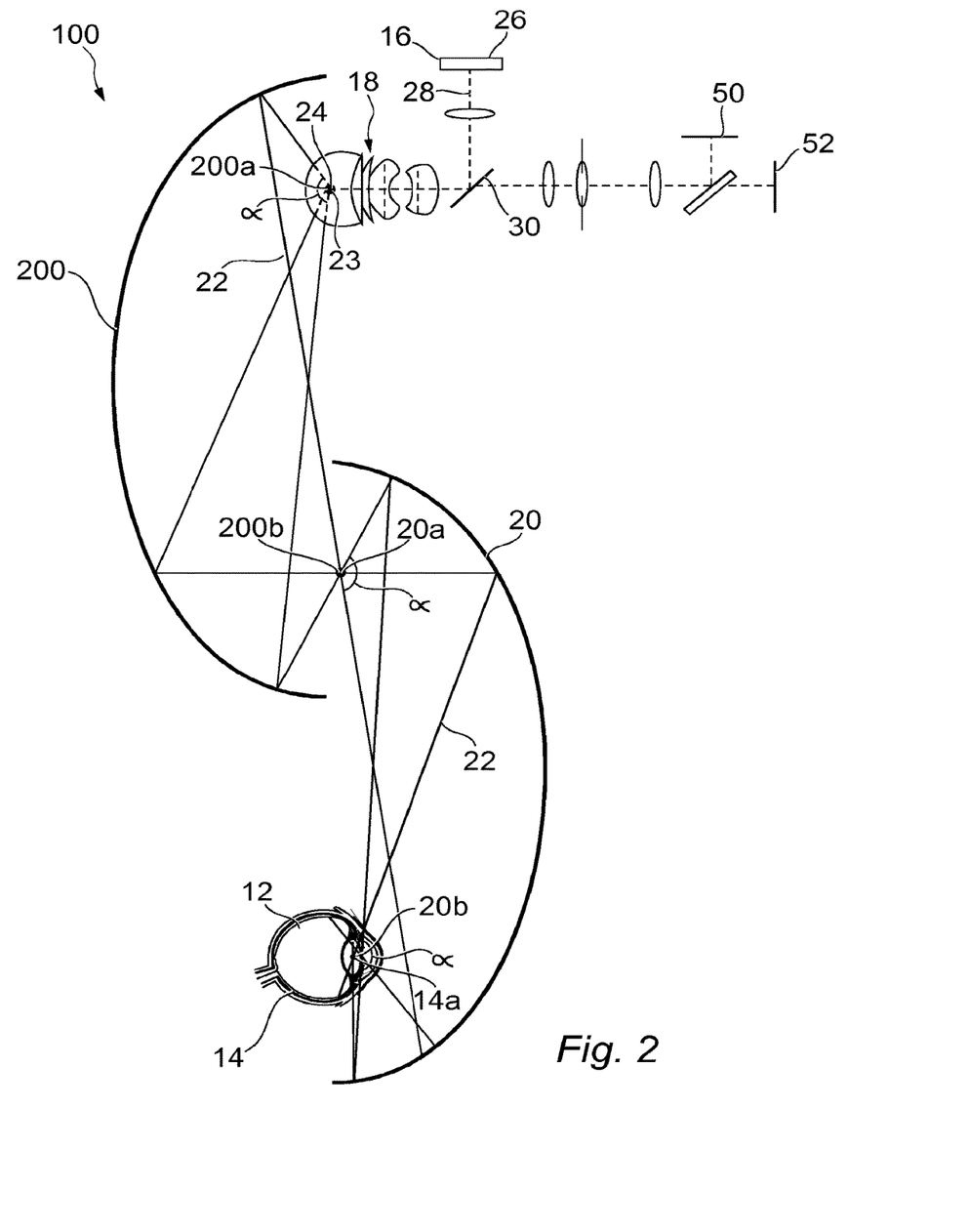
FIG. 2 is a schematic side view of an alternative apparatus for illuminating, imaging and treating the retina of an eye.

FIG. 2 illustrates an alternative embodiment of the apparatus 10. The only difference between the apparatus 10 of FIG. 1 and the apparatus 100 of FIG. 2 is that an illumination relay device 200 has been placed between the lens system 18 and the illumination transfer device 20. The illumination relay device 200 has the same geometry as the illumination transfer device 20.

The illumination relay device 200 has two foci 200a, 200b. In the embodiment illustrated and described here the illumination relay device 200 is an ellipsoidal mirror. However, it should be appreciated that the illumination relay device 200 may alternatively comprise a tilted spherical mirror, an aspherical mirror, an elliptical mirror, an ellipsoidal mirror, a pair of parabola mirrors, a pair of paraboloidal mirrors or a lens system. In the case where the illumination transfer device comprises a lens system, the lens system is arranged to provide two foci.

As illustrated in FIG. 2, the illumination relay device 200, the illumination transfer device 20 and the lens system 18 are arranged such that the apparent point source 24 is provided at the first focus point 200a of the illumination relay device 200 and the second focus point 200b of the illumination relay device 200 is coincident with the first focus point 20a of the illumination transfer device 20. The subject's eye 14 is accommodated at the second focus point 20b of the illumination transfer device 20 as before.

The incident illumination 22 is conveyed to the subject's eye 14 via the illumination relay device 200 and the illumination transfer device 20. The incident illumination 22 provided at the apparent point source 24 by the illumination device 16 and the lens system 18 is coupled by the illumination relay device 200 to the illumination transfer device 20, which, in turn, couples the incident illumination 22 through the pupillary point 14a of the subject's eye 14 to the retina 12, as before.

Given that the illumination relay device 200 has the same geometry as the illumination transfer device 20, the illumination relay device 200 therefore also provides point-to-point transfer of the incident illumination 22 without translation, or clipping, thereof. Therefore, the incident illumination 22 emerging at the second focus point 200b of the illumination relay device 200 emanates therefrom with the same angle α that the incident illumination emanates from the first focus point 200a of the illumination relay device 200. It therefore follows that the incident illumination 22 emanating from the first focus point 20a of the illumination transfer device 20 (or second focus point 200b of the illumination relay device 200) emanates with the same angle α as the incident illumination 22 emanating from the second focus point 20b of the illumination transfer device 20 into the eye 14, as before. The incident illumination 22 therefore again enters the eye 14 without being clipped, thus maximising the area of the retina 12 that can be illuminated by the apparatus 10. The apparatus 100 again provides a 120 degree external angle (200 degree internal angle) of illumination of the retina, as before.

The illumination relay device 200 has a major axis, which lies on a line joining the two foci (200a, 200b). The illumination transfer device 20 also has a major axis, which lies on a line joining the two foci (20a, 20b). The illumination transfer device 20 and the illumination relay device 200 may be arranged such that the major axes of each device are parallel and/or collinear.

The purpose of the illumination relay device 200 is to correct for distortions introduced by the illumination transfer device 20. Since the geometry of the illumination relay device 200 is the same as the geometry of the illumination transfer device 20 the distortions can be cancelled out, or at least partially corrected for. The arrangement of the illumination relay device 200 and the illumination transfer device 20 is such that the major axis (i.e. the line joining the two foci of the device) of the illumination relay device 200 is parallel and collinear to the major axis of the illumination transfer device 20. In this arrangement the distortions are cancelled by symmetry.

The apparatus 10 may also comprise a distortion correction device, which may be part of the data processing device, for correcting distortions introduced by the illumination transfer device 20.

The reflected light returned from the retina 12 is detected in the same manner as described above in relation to the apparatus 10 of FIG. 1. The apparatus 100 is therefore capable of imaging the retina 12 of the eye 14 in the same manner as described above in relation to apparatus 10.

Although the apparatus 10, 100 has been illustrated and described above as being used to illuminate and image the retina 12 of a single eye 14 of a subject, it should be appreciated that the apparatus 10, 100 may be pivotable between a first position, in which the apparatus 10, 100 may be used to illuminate and image the first retina of a first eye, and a second position, in which the apparatus 10, 100 may be used to illuminate and image the second retina of a second eye. In this arrangement the apparatus 10, 100 may be used to illuminate and image both eyes of a subject without the need to move the subject. Alternatively, there may be provided a system for illuminating and imaging the retina of each eye of the patient, whereby the system comprises two apparatuses 10, 100, with each apparatus 10, 100 being used to illuminate and image an eye of the subject.

Although the apparatus 10, 100 has been described above as being used to illuminate and image the retina 12 of the eye 14, it should be appreciated that the apparatus 10, 100 may not necessarily need to produce an image of the retina 12. That is, the apparatus 10, 100 may be used to simply illuminate the retina 12 without acquiring an image, i.e. not detecting the reflected light from the retina 12. The apparatus 10, 100 may therefore be used to treat the retina 12 of the eye 14 by illuminating the retina 12 with light.

The apparatus 10, 100 of the present invention can be manufactured at a lower cost than known retinal imaging apparatuses, such as scanning laser ophthalmoscopes (SLOs), as the apparatus 10, 100 does not require conventional separated laser scanning elements (i.e. two separate one-dimensional scanning elements separated in space from one another, such as a horizontal scanning polygon mirror and a vertical scanning galvanometer scanner). Although, as described above, the apparatus 10, 100 may use such scanning elements. The apparatus 10, 100 can be made more compact than known retinal imaging apparatuses, since the apparatus 10, 100 uses a smaller number of components. The apparatus 10, 100 of the present invention also includes a smaller number of optical surfaces, which increases the optical efficiency of the apparatus 10, 100. The result of this is that, for the same amount of input power to the eye, the total power at the imaging detector is higher than known methods. Providing a wide-angle lens system 18 in combination with an illumination transfer device 20, as described above, allows the incident illumination 22 to be provided indirectly to the pupillary point 14a of the eye 14. This allows use of a wide-angle lens system where the "apparent" point source of incident illumination is located within the lens system itself to provide wide-field illumination of the retina. The apparatus 10, 100 of the present invention thus avoids the need for physical contact with the eye 14. This is advantageous, as patients often find physical contact with retinal illumination apparatuses extremely difficult.

Modifications and improvements may be made to the above without departing from the scope of the present invention. For example, although the illumination device 16 has been described above as including a light source 26 which provides a "flood illumination" to the retina, i.e. the illumination device 16 simultaneously illuminates the area of the retina 12, it should be appreciated that alternatively, or additionally, the illumination device 16 may include a two-dimensional scanning device for scanning the retina 12 of the eye 14 with collimated light. In such a configuration the illumination device 16 and the lens system 18 combine to provide a two-dimensional collimated light scan from the apparent point source 24 located within the lens system 18. The two-dimensional scanning device may comprise a first scanning element and a second scanning element. The first and second scanning elements may comprise an oscillating mechanism. The oscillating mechanism may be a resonant scanner. The first and second scanning elements may comprise an oscillating plane mirror. The oscillating plane mirror may be a galvanometer mirror. The first and second scanning elements may comprise a rotating mechanism. The rotating mechanism may be a rotating polygon mirror. The first and second scanning elements may comprise a line scanning element. The line scanning element may comprise a laser line scanner. The laser line may be generated by a diffractive optical element, cylindrical lens, or other known means of creating a laser line. The first and second scanning elements may comprise a combination of oscillating mechanisms, rotating mechanisms or line scanning elements, as described above. Alternatively, the two-dimensional scanning device may be a microelectromechanical system (MEMS) scanning element having two axes of rotation. However, it should be appreciated that the two-dimensional scanning device may be any suitable device which is capable of rotating in at least two axes, which are preferably orthogonal. The scanning device should preferably be capable of operating at high speed (i.e. above 5 kHz) and provide a high amplitude of scan (i.e. up to 180 degrees or more). In this arrangement the apparatus 10, 100 would illuminate the retina 12 of the eye 14 by scanning the collimated light across the retina. In this arrangement the wavelength and power levels and variability of the collimated light from the scanning device may be the same as described for the flood illumination device. The reflected collimated light may be detected in the manner described above to produce an image of the retina 12.

Furthermore, although the apparatus 10, 100 has been illustrated and described above as comprising one illumination device 16, it should be appreciated that the apparatus 10, 100 may comprise one or more illumination devices, which may include one or more light sources and/or one or more two-dimensional scanning devices.

Also, although the apparent focus point 23 and apparent point source 24 have been illustrated and described above as being located within the outermost lens element 18a of the lens system 18, it should be appreciated that, depending on the arrangement of the lens system 18, the apparent focus point 23 and apparent point source 24 could be located in one of the other lens elements 18b to 18e.

Furthermore, although the FOV of the lens system 18 has been described above as being around 120 degrees, it should be appreciated that the FOV of the lens system 18 could be any suitable angle between 30 and 180 degrees, for example: 40, 50, 60, 70, 80, 90, 100, 110, 120, 130, 140, 150, 160 or 170, or any value in between these angles.

Also, although the apparatus 100 has been illustrated and described above with the illumination relay device 200 being positioned between the lens system 18 and the illumination transfer device 20, it should be appreciated that, since the illumination relay device 200 is essentially identical to the illumination transfer device 20, the apparatus 100 may be considered has having an illumination relay device 200 being positioned between the illumination transfer device 20 and the eye 14.

Furthermore, although the apparatus 10, 100 has been described above as being used to illuminate and/or image the retina 12 of the eye 14, it should be appreciated that the apparatus 10, 100 could be used to treat the retina of the eye by illuminating the retina with collimated light. In this arrangement, the illumination device 16 would include a source of collimated light which may be operated to produce a laser beam of variable wavelength and/or power. Furthermore, the source of collimated light may be operated to produce a number of differing wavelengths, if required. This allows the apparatus 10, 100 to treat retinal diseases.

Also, although not illustrated or described above, it should be appreciated that, in order to minimise back reflections from the lens system 18, the light source 26 would be polarised and the return optical path 30 would include a polariser either before or after the aperture 46, or alternatively, two separate polarisers before the first and second detectors 50, 52. In this arrangement the polarisers would block the light directly reflected from the lens system 18 that is not randomly polarised.

Furthermore, although not illustrated or described above, it should be appreciated that the lens system 18 and/or the illumination transfer device 20, 200 may be moveable. That is, the lens system 18 and/or the illumination transfer device 20, 200 may be moveable relative to one another to compensate for movement in the location of the apparent focus point 23 and apparent point source 24 in the lens system 18 when illuminating and/or imaging the retina 12 at different FOV angles. When illuminating and/or imaging the retina 12 at different FOV angles, for example when illuminating and/or imaging the fundus area of the retina 12 and then illuminating and/or imaging the peripheral of the retina 12, the apparent focus point 23 and apparent point source 24 in the lens system 18 may move slightly depending on the FOV angle. Arranging the lens system 18 and/or the illumination transfer device 20, 200 such that they may be moveable with respect to one another ensures that the apparent focus point 23 and apparent point source 24 of the lens system 18 are always accommodated at the first focus point 20a, 200a of the illumination transfer device 20, 200. As described above, this prevents the incident illumination 22 being clipped by the iris when entering the eye.

The invention claimed is:

1. An apparatus for illuminating a retina of an eye, the apparatus comprising:
    an illumination device;
    a wide-angle lens system,
    wherein the illumination device and the wide-angle lens system combine to provide incident illumination from an apparent point source located within the wide-angle lens system; and
    an illumination transfer device, wherein the illumination transfer device has a first focus point and a second focus point, and the apparent point source of the wide-angle lens system is provided at the first focus point of the illumination transfer device and the eye is accommodated at the second focus point of the illumination transfer device;
    wherein the illumination transfer device transfers the incident illumination from the apparent point source into the eye to illuminate the retina, wherein the incident illumination travels directly from the apparent point source to a point on the illumination transfer device and directly from the point on the illumination transfer device to the second focus point of the illumination transfer device at which the eye is accommodated,
    wherein the apparatus comprises an apparent focus point located within the wide-angle lens system, and
    wherein the apparent focus point and the apparent point source are coincident.

2. The apparatus according to claim 1, wherein the illumination device and the lens system are arranged to illuminate an area of the retina.

3. The apparatus according to claim 1, wherein the wide-angle lens system includes a wide-angle lens having a field of view (FOV) of between 100 degrees and 180 degrees.

4. The apparatus according to claim 3, wherein the illumination transfer device comprises one of the group consisting of a tilted spherical mirror, an aspherical mirror, an elliptical mirror, an ellipsoidal mirror, a pair of parabola mirrors, a pair of paraboloidal mirrors, and a second lens system comprising two foci, and wherein the illumination transfer device is shaped and positioned relative to the apparent point source of the wide-angle lens to transfer the incident illumination from the apparent point source into the eye to illuminate the retina.

5. The apparatus according to claim 1, wherein the illumination device includes a light source adapted to provide light at a power of between 500 nWatt and 1 W.

6. The apparatus according to claim 1, wherein the illumination device includes a light source comprising one of the group consisting of a laser, a light emitting diode (LED), a Vertical Cavity Surface Emitting Laser (VCSEL), a super luminescent diode (SLD), a diode laser, a collimated incandescent lamp, a flash or illumination device, or a digital light processing (DLP) projection device.

7. The apparatus according to claim 1, wherein the illumination device includes comprises a two-dimensional scanning device for scanning the retina of the eye with collimated light such that the illumination device and the wide-angle lens system are arranged to provide a two-dimensional collimated light scan from the apparent point source located within the wide-angle lens system.

8. The apparatus according to claim 7, wherein the two-dimensional scanning device comprises at least one of a single scanning element capable of rotating in at least two axes or and two separate scanning elements each having a single axis of rotation.

9. The apparatus according to claim 8, wherein the single scanning element is a microelectromechanical (MEMS) scanning element.

10. The apparatus according to claim 1, comprising one or more detectors for detecting the reflected light from the retina.

11. A method of illuminating a retina of an eye, the method comprising:
providing an illumination device;
providing a wide-angle lens system;
using the illumination device and the wide-angle lens system in combination to provide incident illumination from an apparent point source located within the wide-angle lens system;
providing an illumination transfer device having a first focus point and a second focus point;
providing the apparent point source at the first focus point of the illumination transfer device and the eye at the second focus point of the illumination transfer device;
using the illumination transfer device to transfer the incident illumination from the apparent point source into the eye to illuminate the retina, wherein the incident illumination travels directly from the apparent point source to a point on the illumination transfer device and directly from the point on the illumination transfer device to the second focus point of the illumination transfer device at which the eye is accommodated;
wherein the apparatus comprises an apparent focus point located within the wide-angle lens system, and
wherein the apparent focus point and the apparent point source are coincident.

12. The method according to claim 11, wherein the illumination device and the wide-angle lens system are arranged to illuminate an area of the retina.

13. The method according to claim 11, wherein the wide-angle lens system includes a wide-angle lens having a field of view (FOV) of between 100 degrees and 180 degrees.

14. The method according to claim 11 comprising providing one or more detectors to detect reflected light from the retina to form an image of the retina.

* * * * *